United States Patent [19]

Peck

[11] 4,322,438

[45] Mar. 30, 1982

[54] METHOD FOR THE USE OF ORALLY ADMINISTERED 13-CIS-RETINOIC ACID IN THE TREATMENT OF ACNE

[75] Inventor: Gary L. Peck, Silver Spring, Md.

[73] Assignee: United States of America, Washington, D.C.

[21] Appl. No.: 175,594

[22] Filed: Aug. 5, 1980

Related U.S. Application Data

[63] Continuation-in-part of Ser. No. 63,770, Aug. 6, 1979, abandoned.

[51] Int. Cl.³ .............................................. A61K 31/20
[52] U.S. Cl. ..................................... 424/318; 424/344
[58] Field of Search ................................. 424/318, 344

[56] References Cited

FOREIGN PATENT DOCUMENTS

70/4566  6/1970  South Africa .
71/0145  1/1971  South Africa .

OTHER PUBLICATIONS

Strauss et al., J. Invest. Dermatol., 70:228; 4-1978.
Gunby-J.A.M.A., 240:7,610, 8/18/78.
Investigative Drug Brochure, Ro-4-3780, (Hoffman LaRoche, Inc.), 2-1978.
New England Journal of Medicine, vol. 300, No. 7, pp. 329-333 & 359-360, (2-1979).
J.A.M.A., vol. 240, No. 7, p. 610, (8-1978).
Demratologica, 157 (Suppl. 1): 11-12, (1978).
Ophthalmology 85:35, (7-1978).

Primary Examiner—Leonard Schenkman
Attorney, Agent, or Firm—Holman & Stern

[57] ABSTRACT

In a method of alleviating nodulocystic and conglobate acne in humans by the oral administration of 13-cis-retinoic acid, the improvement comprising: administering the 13-cis-retinoic acid in a high dosage of from 1.0 to 2.0 mg/kg/day for from 2 to 4 weeks; and reducing the amount of 13-cis-retinoic acid to a low dosage of from 0.25 to 0.5 mg/kg/day for a period of from 12 to 14 weeks, so that the total treatment period is about 16 weeks.

8 Claims, No Drawings

METHOD FOR THE USE OF ORALLY ADMINISTERED 13-CIS-RETINOIC ACID IN THE TREATMENT OF ACNE

This is a continuation-in-part of application Ser. No. 63,770 filed Aug. 6, 1979, now abandoned.

BACKGROUND OF THE INVENTION

1. Field of the Invention

Retinol (vitamin A) and retinoic acid (vitamin A acid), its isomers, and certain of its analogs are known to have beneficial effects in the treatment of acne and keratinizing skin disorders.

Acne affects large patient populations and is a common inflammatory skin disorder which usually localizes on the face. Fortunately, the disease usually disappears and in the interval of months or years between onset and resolution, therapy, although not curative, can satisfactorily suppress the disease in the majority of patients.

A small number of acne patients with severe disease show little or no response to intensive therapeutic efforts including the use of high doses of oral tetracycline, dapsone, prednisone and, in women, estrogen. In many cases, these drugs afford only a modest degree of control while the side effects of these agents severely restrict their usefulness. Patients with nodulocystic acne suffer from large, inflammatory, suppurative nodules appearing on the face, and frequently the back and chest. In addition to their appearance, the lesions are tender and often purulently exudative and hemorrhagic. Disfiguring scars are frequently inevitable.

Therapies for acne involve local and systemic administration of vitamin A compounds, collectively known as retinoids. Topical application of all-trans retinoic acid has been tried with some success, particularly against comedones or blackheads, but this condition frequently returns when the treatment is withdrawn. Additionally, retinoic acid applied topically can be highly irritating and its use can be painful for the patient depending on the concentration used and the frequency of application.

A number of side effects complicates the administration of large doses of vitamin A. Among the many symptoms of hypervitaminosis A are weight loss, desquamation of the skin, hair loss, irritation of the oral and pharyngeal mucosa, and nose bleeds, headaches, bone pain, liver toxicity due to storage of vitamin A in the liver, papilledena, pseudotumor cerebri, demineralization and periosteal thickening of bones. Because of these and other side effects oral treatment with vitamin A and all-trans retinoic acid, which produces similar side effects, is rarely recommended for dermatopathic conditions.

The present invention relates to an improved method of use of orally administered 13-cis-retinoic acid which unexpectedly results in the virtual elimination of severe chronic nodulocystic and conglobate acne, while at the same time it markedly reduces the side effects conventionally associated with oral retinoic acid therapies.

2. Description of the Prior Art

The successful use of 13-cis-retinoic acid, administered orally, for the treatment of cystic and conglobate acne was reported in Peck, et., "Prolonged Remissions of Cystic and Conglobate Acne with 13-cis-Retinoic Acid", New Eng. J. Med. 300:329–333 and 30:359–360, Feb. 15, 1979. In this study, a four month course of therapy with oral 13-cis-retinoic acid was begun at a minimum divided dosage of 1.0 mg per kilogram of body weight per day. The dosage was then increased in increments of 0.5 to 1.0 mg/kg/day at intervals of two to four weeks until either an appreciable therapeutic effect or dose-limiting toxicity was observed.

A report of the above study is also found in Gunby, "Synthetic Retinoid Used In Dermatopathies", J.A.M.A. 240:610, Aug. 18, 1978. In this report, it is further stated that the oral dosages used were from 80 to 240 mg/day of 13-cis-retinoic acid in capsule form with an average dose of 140 mg/day. Still another report of this study will be found in Peck, et al., "Treatment of Darier's Disease, Lamellar Ichthyosis, Pityriasis Rubra Pilaris, Cystic Acne and Basal Cell Carcinoma with Oral 13-cis-Retinoic Acid", Dermat. 157 (Suppl. 1):11–12 (1978).

Belgian Pat. No. 762,344 of Aug. 2, 1971, also discloses the use of orally administered 13-cis-retinoic acid for the treatment of acne (unspecified) and psoriasis. However, only a general dosage for various vitamin A compounds of from 0.1 mg to 0.5 mg to about 3.0 mg per kilogram of body weight is disclosed. Moreover, there is no example directed towards the use of 13-cis-retinoic acid.

In "Investigational Drug Brochure RO4-3780", printed by Hoffman-LaRoche Inc. sometime prior to the studies leading to the present invention, there appear several general statements indicating that all-trans retinoic acid had been used for oral treatment of acne, and that 13-cis-retinoic acid had proved to be less toxic than all-trans retinoic acid in animal experiments. There is also the statement that: "Skin diseases characterized by accelerated or pathological keratinization may respond to treatment with RO4-3780 (sic: 13-cis-retinoic acid), . . . as well as acne.". However, dosages were not discussed.

In a later edition of "Investigational Drug Brochure RO4-3780", Feb. 1978, there are statements mostly based upon the same studies that were the basis for U.S. patent application Ser. No. 63,770 filed Aug. 6, 1979. Specifically, it is disclosed that interest in the therapeutic applications of 13-cis-retinoic acid developed when preliminary testing indicated that it had epithelium-protecting ability equivalent to retinoic acid and was apparently less toxic. There is a further disclosure of the treatment of an unspecified acne with 13-cis-retinoic acid administered orally, but with no indication of the method of varying dosage which is the subject of this invention.

The "Handbook of Nonprescription Drugs", 5th ed., 1977, A.P.A. pub., Pp 140, 319, 320, discloses the use of vitamin A and retinoic acid, but not the 13-cis-stereoisomer, in the treatment of acne (unspecified). However, the disclosure of this publication is opposite to that of the subject invention, in that it states: "The systemic use of vitamin A for the treatment of acne, . . . is not warranted by clinical evidence." at page 140; and that: "Treatments that have been abandoned or have not been proved effective include oral vitamin A, . . . " at page 320.

J. V. Straumford reported a systemic usage of large oral doses of retinol, the alcohol form of vitamin A, over a long period of time for the treatment of acne (Straumford, J. V., "Vitamin A: Its Effect on Acne", Northwest Med., 42:219:255, August 1943). These results however have been disputed and systemic therapy of acne utilizing retinol has been challenged by other investigators (Anderson, J. A. D., et al., "Vitamin A in Acne Vulgaris", Brit. Med. J., 2:294–296, August, 1963; Lynch, F. W., et al., "Acne Vulgaris Treated with Vitamin A", Arch. Derm. 55:355, 357, March 1947; and Mitchell, G. H., et al., "Results of Treatment of Acne Vulgaris by Intramuscular Injections of Vitamin A", Arch. Derm. 64:428–434, October 1951).

Topical administration of retinoic acid for the treatment of acne was reported by Kligman, et al., (Arch. Derm. 99:469–476, 1969, U.S. Pat. No. 3,729,568). The effectiveness of this treatment as disclosed by Kligman is often associated with a noticeable irritating effect of topically applied retinoic acid.

The process for treating acne vulgaris topically utilizing retinal, the aldehyde form of vitamin A, is disclosed in U.S. Pat. No. 3,932,665. The aldehyde form, unlike the acid form of vitamin A, exerts its therapeutic effect without producing irritation, inflammation, erythema, or peeling of the skin. This patent also discloses the topical use of 13-cis-retinal in the treatment of acne vulgaris.

The method of treating acne with C-20 and C-22 vinylogs of desmethyl retinoic acid is disclosed in U.S. Pat. No. 3,882,244. These vinylogs as disclosed in the patent are applied topically to the site of the acne infection as a solution, ointment or powder. The treatment of acne vulgaris with retinoic acid analogs particularly 11-(2',6',6'-trimethylcyclohex-1'-enyl-1')-5,9-dimethylundeca-2,4,6,8,10-pentenoic acid is disclosed in U.S. Pat. No. 3,934,028. This compound can be used either internally or topically. When taken orally, the daily dosage of this compound ranged from 30–300 mg taken over from 2 to 8 weeks. However, there is no indication that the compounds leads to remission from the disease after administration of the compound is withdrawn.

Although 13-cis-retinoic acid is generally less toxic than all-trans retinoic acid, there are still precautions that must be observed in its use. With oral retinoic acid, headaches, nausea, vomiting, and some of the skin and mucous membrane lesions experienced with hypervitaminosis A have been reported. Because of chemical and pharmacological similarities between 13-cis-retinoic acid, retinoic acid and retinol, similar adverse reactions occur with 13-cis-retinoic acid. See Blackman, et al., "Blepharoconjunctivitis: Side Effect of Oral 13-cis-Retinoic Acid Therapy of Dermatologic Disease", Ophthal. 85:35, July 1978, and some of the above articles.

SUMMARY OF THE INVENTION

This invention provides an improved method of treating nodulocystic and conglobate acne in human beings by oral administration of 13-cis-retinoic acid in amounts and for periods of time which afford an effectively complete remission from the condition even after administration of the compound ceases.

The improvement of this invention over the prior art, is the use of a "high-low" oral dosage schedule, which unexpectedly is able effectively to treat cystic acne, while remarkably reducing the toxic effects of the 13-cis-retinoic acid. Because the conventional treatment with 13-cis-retinoic acid, as disclosed in the prior art, was to increase the dosage when the number of cysts on a patient was not reduced, it was totally unexpected that the dosage regimen of this invention would be effective. Not only were the results using the improved method of this invention as good as the prior art, but they also were accomplished with minimization of the usual toxic effects which include chapped lips, moderate chapping of the facial and body skin and dryness of the nasal mucosa with mild nose bleeds.

Specifically, the invention relates to a method of administering 13-cis-retinoic acid at a dose level which preserves the beneficial effects of clearing nodulocystic and conglobate acne, while at the same time, minimizes or effectively eliminates the undesirable side effects usually associated with administration of large doses of vitamin A.

An unexpected aspect of this invention is that 13-cis-retinoic acid, unlike all-trans retinoic acid, the naturally occurring form, exerts its therapeutic effects in the case of nodulocystic acne even after administration of the compound has stopped. Complete clearing has persisted for as long as 41 months after cessation of administration of the drug. The entire treatment may be repeated at any time thereafter.

Accordingly, this invention provides a relatively non-toxic dose level and dose schedule of 13-cis-retinoic acid for treatment of nodulocystic and conglobate acne.

DESCRIPTION OF PREFERRED EMBODIMENTS

Regimens are provided for treating nodulocystic and conglobate acne with oral 13-cis-retinoic acid. The regimens provide the minimum dose for a patient which effectively eliminates nodulocystic and conglobate acne while at the same time minimizes the undesirable side effects such as irritation of the mucosa, chapping of the skin, and nose bleeds, usually associated with the systemic administration of retinoic acid isomers and analogs.

The improved method according to this invention contemplates a primary treatment period of approximately sixteen weeks. During the first part of this period, usually about four weeks, 13-cis-retinoic acid is orally administered at a "high" daily dosage, preferably of approximately 2.0 milligrams per kilogram of body weight (mg/kg). During the second part of this period, usually about twelve weeks, 13-cis-retinoic acid is orally administered at a "low" daily dosage, preferably of approximately 0.5 mg/kg. It is critical that the reduced dosage, once started, be continued even though the number of cysts on a patient increases or is not decreased. It was a consistent but unexpected finding that even those patients who failed to experience a decrease in the number of their cysts at the time the "high" dose was terminated, did subsequently respond well while taking the "low" dose. Although some of the symptoms of acute toxicity may appear during the "high" dosage part of the treatment, they generally disappear during the "low" dosage part. Moreover, and also very unexpectedly, after the oral dosage is completed, the patients continue to experience the beneficial effects of the 13-cis-retinoic acid. Thus, the cysts on patients continue to disappear even after the primary treatment period is completed. Where cysts persist even several months after the primary treatment period is completed, or where they reoccur after several months, a secondary and/or tertiary treatment period duplicating the primary treatment period in dosage and time may be instituted.

In a further refinement of the improved method of this invention, one may distinguish between facial acne and acne on the trunk.

Facial acne is generally less severe, or at least more easily treated. For this reason, a "high" dosage of as low as about 1.0 mg/kg may be administered for as short as a two week first part, with a "low" dosage of as low as 0.25 mg/kg administered for the remaining part of the sixteen week period.

In trunk acne, the "high" dosage first part of the period may be as short as two weeks, with the "low" dosage for the remaining part of the sixteen week period.

The following comparative example is illustrative of a method of oral 13-cis-retinoic acid administration which was disclosed in the prior art.

Comparative Example

In a series of 33 patients with severe, treatment-resistant, cystic acne, oral 13-cis-retinoic acid was given at a beginning dosage of 0.5 mg/kg/day for a period of 4 months. The patients were examined every 4 weeks and the number of acne cysts remaining determined. If the examination revealed an increase in the number of acne cysts, the dosage was increased an additional 0.5 to 1.0 mg/kg/day for the next 4 week period. The final average maximum dose in this study was 1.5 mg/kg/day. Therapy was stopped in all patients at four months regardless of the therapeutic response observed. Two months after the termination of oral 13-cis-retinoic acid administration, the patients were re-examined. Patients showing persistent acne cysts were administered a second course of treatment with oral 13-cis-retinoic acid in the same manner as the first treatment. 15 patients received a second course of therapy beginning two months after discontinuation of the first course. Of interest is that only 1 patient of the 33 cleared completely during the initial course of therapy. However, 21 additional patients cleared completely at times varying from 1-10 months post-treatment.

Of the original group, 22 patients cleared completely; 9 patients cleared all but 3 or less cysts; the most severely afflicted patient of the group showed an 86% improvement reducing the number of cysts from 181 at the start of the study to 24 at the end. This latter patient, after expressing satisfaction with his improvement, withdrew from further treatment. The remaining patient was dropped from the study for treatment of an unrelated infection. This study demonstrates the delayed beneficial effect of the drug.

The following studies are illustrative of the "High-Low" dosage regimen according to the improved method of this invention.

EXAMPLE 1—"High-Low" Dosage

In a first study of two patients, a dosage schedule which which reduced toxicity but did not reduce the beneficial effects of the drug was used. Specifically, the patients were treated at a dosage of 2.0 mg/kg/day for 4 weeks. The dosage was reduced to 0.5 mg/kg/day for 12 weeks thereafter.

The first patient had 28 acne cysts prior to treatment. At the 4 week visit during treatment, he developed the usual acute toxicity: chapped lips, moderate chapping of the facial and body skin, and dryness of the nasal mucosa with mild nose bleeds. The dosage was reduced at that point and at the 10 week visit during treatment, only 4 acne cysts were present, the toxicity had lessened in that the nose bleeds had stopped, and the other side effects had gone from moderate severity to mild. At the 8 week post-treatment visit he still had 5 lesions but there were no side effects. At the 14 week post-treatment visit he only had one lesion without having received any further therapy.

The second patient had 13 cysts prior to treatment. At his 4 week visit during treatment, he had the same side effects as the first patient, but he still had 13 cysts. In spite of this failure to reduce the number of acne cysts, the dosage was lowered from 2.0 to 5.0 mg/kg/day. At the 8 week visit during treatment, all side effects except mild chapping of the lips had disappeared, but he now had 16 cysts. The dosage was maintained at 0.5 mg/kg/day. At the 11 week visit during treatment, the number of cysts had decreased to 9 and at the 16 week visit only 2 cysts were present. By 10 weeks post-treatment, the patient was entirely free of acne cysts.

The patients had prolonged remissions of at least 17 and 22 months without the need for further therapy.

EXAMPLE 2—Reduced "High-Low" Dosage

A second study was conducted using orally administered 13-cis-retinoic acid with an initial patient group of forty. These were divided into two groups of twenty each; group (A) had 60% or more of their acne cysts on the face, group (B) has 60% or more of their acne cysts on the trunk.

(A) In the facial acne group, the "high" daily dose was 1.0 mg/kg, given to 10 patients for 2 weeks and to 10 patients for 4 weeks. The "low" daily dose was 0.25 mg/kg given for the remainder of a sixteen week treatment period for all patients. The results of this treatment are shown below in Tables A.

TABLES A

| Weeks of Treatment | | 0 | 1 | 2 | 4 | 8 | 12 | 16 | * |
|---|---|---|---|---|---|---|---|---|---|
| | | | | Facial Group | | | | | |
| | | | | (i) all lesions | | | | | |
| Entire Group (20 Patients) | Average Cysts Per Patient | 22.05 | 22.65 | 25.0 | 20.5 | 12.35 | 9.35 | 6.5 | 5.7 |
| | Improvement (percentage) | — | −2.7 | −13.4 | 7 | 44 | 58 | 71 | 74 |
| 2-Week Group (10 Patients) | Average Cysts Per Patient | 19.8 | 20.0 | 22.4 | 17.7 | 12.2 | 8.5 | 6.0 | 7.0 |
| | Improvement (percentage) | — | −1 | −13 | 11 | 38 | 57 | 70 | 65 |
| 4-Week Group (10 Patients) | Average Cysts Per Patient | 24.3 | 25.3 | 27.6 | 23.3 | 12.5 | 10.2 | 7.0 | 4.4 |
| | Improvement (percentage) | — | −4 | −14 | 4 | 49 | 58 | 71 | 82 |
| | | | | (ii) facial lesions only | | | | | |
| Entire Group (20 | Average Cysts Per Patient | 17.6 | 17.4 | 19.1 | 13.4 | 8.0 | 5.25 | 2.7 | 2.2 |
| | Improvement | — | 1 | −9 | 24 | 55 | 70 | 85 | 87 |

TABLES A-continued

| Weeks of Treatment | | 0 | Facial Group 1 | 2 | 4 | 8 | 12 | 16 | * |
|---|---|---|---|---|---|---|---|---|---|
| Patients) | (percentage) | | | | | | | | |
| 2-Week Group (10 Patients) | Average Cysts Per Patient | 15.4 | 14.4 | 15.8 | 10.2 | 7.3 | 4.3 | 1.9 | 2.3 |
| | Improvement (percentage) | — | 6 | −3 | 34 | 53 | 72 | 88 | 85 |
| 4-Week Group (10 Patients) | Average Cysts Per Patient | 19.8 | 20.4 | 22.4 | 16.6 | 8.7 | 6.2 | 3.5 | 2.1 |
| | Improvement (percentage) | — | −3 | −13 | 16 | 56 | 69 | 82 | 89 |

*4 Weeks Post Treatment (B) In the trunk acne group, the "high" daily dose was 2.0 mg/kg, given to 10 patients for 2 weeks and to 10 patients for 4 weeks. The "low" daily dose was 0.5 mg/kg given for the remainder of a sixteen week treatment period for all patients. The results of this treatment are shown below in Tables B.

TABLES B

| Weeks of Treatment | | 0 | Trunk Group 1 | 2 | 4 | 8 | 12 | 16 | * |
|---|---|---|---|---|---|---|---|---|---|
| (i) all lesions | | | | | | | | | |
| Entire Group (20 Patients) | Average Cysts Per Patient | 42.7 | 39.3 | 38.9 | 28.3 | 19.8 | 16.9 | 11.5 | 8.3 (1) |
| | Improvement (percentage) | — | 8 | 9 | 34 | 54 | 61 | 73 | 81 (1) |
| 2-Week Group (10 Patients) | Average Cysts Per Patient | 42.8 | 43.0 | 41.2 | 29.8 | 20.1 | 14.8 | 7.9 | 6.7 (2) |
| | Improvement (percentage) | — | 0 | 4 | 30 | 53 | 65 | 82 | 84 (2) |
| 4-Week Group (10 Patients) | Average Cysts Per Patient | 42.6 | 35.6 | 36.5 | 26.7 | 19.4 | 18.9 | 15.1 | 9.8 |
| | Improvement (percentage) | — | 16 | 14 | 37 | 54 | 56 | 65 | 77 |
| (ii) back lesions only | | | | | | | | | |
| Entire Group (20 Patients) | Average Cysts Per Patient | 20.9 | 19.2 | 18.65 | 14.0 | 10.75 | 10.65 | 7.35 | 5.58 (1) |
| | Improvement (percentage) | — | 8 | 11 | 33 | 49 | 49 | 65 | 73 (1) |
| 2-Week Group (10 Patients) | Average Cysts Per Patient | 23.6 | 23.3 | 21.0 | 16.6 | 12.5 | 9.9 | 5.2 | 4.3 (2) |
| | Improvement (percentage) | — | 1 | 11 | 30 | 47 | 58 | 78 | 82 (2) |
| 4-Week Group (10 Patients) | Average Cysts Per Patient | 18.2 | 15.0 | 16.3 | 11.4 | 9.0 | 11.4 | 9.5 | 6.7 |
| | Improvement (percentage) | — | 18 | 10 | 37 | 51 | 37 | 48 | 63 |
| (iii) chest lesions only | | | | | | | | | |
| Entire Group (20 Patients) | Average Cysts Per Patient | 9.65 | 9.05 | 9.45 | 7.4 | 5.8 | 3.9 | 2.8 | 2.16 (1) |
| | Improvement (percentage) | — | 6 | 2 | 23 | 40 | 60 | 71 | 78 (1) |
| 2-Week Group (10 Patients) | Average Cysts Per Patient | 8.8 | 10.2 | 9.8 | 6.7 | 4.3 | 2.9 | 1.9 | 1.89 (2) |
| | Improvement (percentage) | — | −15.9 | −11.4 | 24 | 51 | 67 | 78 | 79 (2) |
| 4-Week Group (10 Patients) | Average Cysts Per Patient | 10.5 | 7.9 | 9.1 | 8.1 | 7.3 | 4.9 | 3.7 | 2.4 |
| | Improvement (percentage) | — | 25 | 13 | 23 | 30 | 53 | 65 | 77 |
| (iv) facial lesions only | | | | | | | | | |
| Entire Group (20 Patients) | Average Cysts Per Patient | 12.15 | 10.15 | 10.65 | 6.85 | 3.3 | 2.3 | 1.35 | 0.58 (1) |
| | Improvement (percentage) | — | 16 | 12 | 44 | 73 | 81 | 89 | 95 (1) |
| 2-Week Group (10 Patients) | Average Cysts Per Patient | 10.4 | 9.5 | 10.4 | 6.5 | 3.3 | 2.0 | 0.8 | 0.44 (2) |
| | Improvement (percentage) | — | 9 | 0 | 37 | 68 | 81 | 92 | 96 (2) |
| 4-Week Group (10 Patients) | Average Cysts Per Patient | 13.9 | 10.8 | 10.9 | 72 | 3.3 | 2.6 | 1.9 | 0.7 |
| | Improvement (percentage) | — | 22 | 22 | 48 | 76 | 81 | 86 | 95 |

*4-Weeks Post Treatment
(1) 19 Patients
(2) 9 Patients

Observations and Conclusion—Example 2

The results of this study are entirely consistent with those of Example 1 and with the improved method of this invention.

In group A (facial acne), the observed lesions (cysts) initially increased for a time prior to the fourth week of treatment, but then steadily decreased. This observed temporary increase may be attributable to the abrupt cessation of partially effective previous therapies. At the end of the fourth week, patients receiving a 2-week high dose appeared slightly more improved than those receiving a 4-week high dose. However, this advantage was nullified in later observations.

In group B (trunk acne) there was no significant difference between the patients receiving a 2-week high dose and those receiving a 4-week high dose. However, it is noted that there is an unexplained difference in results between the 2-week and 4-week high dose patients, after both had been receiving identical dosages for the first two weeks of the primary treatment period. These differences were greatly lessened as the treatment progressed, indicating that they were probably caused by varying rates of patient reaction to the treatment.

Observed symptoms of acute toxicity such as the intensity of chapped lips and dry, red, chapped facial skin markedly decreased after the initial high dosage was lowered.

In evaluating the data in these tables, it must be remembered that the exact percentages are averages and were subject to variation because of the small patient sample, but that the trends of improvement are extremely significant. The "percentage improvement" was in all instances, calculated from a zero base.

General Observations

Although the total length of treatment in the studies herein was 16 weeks, this invention method is not limited to that precise time. In a given individual, a total effective treatment period of as little as 12 weeks or as much as 20 weeks may be required. However, the 16 week period appears to be optimum for practical utilization of this invention, given the present technological inability to predict an individual's optimum total treatment time.

Similarly, the 2-week and 4-week first parts of the treatment period may be varied and still remain within this invention method. In a given individual, a first part effective treatment period of as little as 7 days or as much as 42 days may be required. However, the 2-week to/or 4-week first part of the treatment period appears to be optimum for maximum utilization of this invention, given the present technological inability to predict an individual's optimum first part treatment time.

The dosage of 13-cis-retinoic acid may be slightly varied and still be within the scope of this invention. What cannot be varied is that after the first part of the treatment period, the dosage must be reduced.

I claim:

1. In a method of alleviating nodulocystic and conglobate acne in humans by the oral administration of 13-cis-retinoic acid, the improvement comprising:
   (a) administering 13-cis-retinoic acid in a high dosage of from about 1.0 to about 2.0 milligrams per kilogram of body weight daily for a first period of from about 2 to about 4 weeks; and
   (b) reducing the amount of 13-cis-retinoic acid to a low dosage of from about 0.25 to about 0.5 milligrams per kilogram of body weight daily for a second period of from about 12 to about 14 weeks, for those patients whose acne has not been substantially improved at the end of the first period as measured by the percentage reduction in cysts, so that the total treatment period is about 16 weeks.

2. The improved method of claim 1 wherein the high dosage is administered for about 2 weeks.

3. The improved method of claim 1 wherein the high dosage is administered for about 4 weeks.

4. The improved method of claim 2 or 3 wherein at least 60% of a patient's acne lesions appear on the face and wherein the high dosage is about 1.0 milligrams per kilogram of body weight daily and the low dosage is about 0.25 milligrams per kilogram of body weight daily.

5. The improved method of claim 2 or 3 wherein at least 60% of a patient's acne lesions appear on the trunk and wherein the high dosage is about 2.0 milligrams per kilogram of body weight daily and the low dosage is about 0.5 milligrams per kilogram of body weight daily.

6. In a method of alleviating nodulocystic and conglobate acne in humans by the oral administration of 13-cis-retinoic acid, the improvement comprising:
   (a) administering 13-cis-retinoic acid in a high dosage of about 2.0 milligrams per kilogram of body weight daily for a first period of about 4 weeks;
   (b) reducing the amount of 13-cis-retinoic acid to a low dosage of about 0.5 milligrams per kilogram of body weight daily for a second period of about 12 weeks, for those patients whose acne has not been substantially improved at the end of the first period as measured by the percentage reduction in cysts, so that the total treatment period is about 16 weeks.

7. The improved method of claim 1 or 6 wherein the regimen comprising steps (a) and (b) is repeated up to three times.

8. The improved method of claim 1 or 6 wherein the regimen comprising steps (a) and (b) is repeated upon each reoccurrence of the acne.

* * * * *